United States Patent [19]

Soeda et al.

[11] Patent Number: 5,750,498
[45] Date of Patent: May 12, 1998

[54] TRANSPARENT GELATIN GEL TYPE AIR FRESHENER

[75] Inventors: Takahiko Soeda, Kawasaki; Masahiko Shinohara, Tokyo; Taro Hozumi, Tokyo; Seisuke Sato, Tokyo, all of Japan

[73] Assignees: Ajinomoto Co., Inc.; Nihon Firmenich K.K.; Systems Bio-Industries Co., Ltd., all of Tokyo, Japan

[21] Appl. No.: 703,125

[22] Filed: Aug. 26, 1996

[30] Foreign Application Priority Data

Sep. 6, 1995 [JP] Japan ................... 7-229081

[51] Int. Cl.$^6$ .............. A61K 7/46; B01J 13/00
[52] U.S. Cl. ............ 512/4; 252/315.1; 252/315.3
[58] Field of Search ............ 252/315.1, 315.4; 424/76.4; 512/4

[56] References Cited

U.S. PATENT DOCUMENTS

| | | | |
|---|---|---|---|
| 3,767,787 | 10/1973 | Segal | 424/76.4 |
| 4,453,909 | 6/1984 | Lindauer et al. | 425/511 |
| 5,053,341 | 10/1991 | Companion | 252/315.1 X |
| 5,147,344 | 9/1992 | Sachau et al. | 252/315.1 X |
| 5,156,956 | 10/1992 | Motoki et al. | 435/68.1 |
| 5,518,742 | 5/1996 | Soeda et al. | 426/63 |

FOREIGN PATENT DOCUMENTS

| | | |
|---|---|---|
| 0 152 982 | 8/1985 | European Pat. Off. . |
| 0 328 702 | 8/1989 | European Pat. Off. . |
| 0 631 788 | 1/1995 | European Pat. Off. . |
| 2 659 352 | 9/1991 | France . |
| 54-135229 | 10/1979 | Japan . |
| 55-81655 | 6/1980 | Japan . |
| 1-119258 | 5/1989 | Japan . |
| 710 881 | 6/1954 | United Kingdom . |
| 938 039 | 9/1963 | United Kingdom . |

*Primary Examiner*—Richard D. Lovering
*Attorney, Agent, or Firm*—Oblon, Spivak, McClelland, Maier & Neustadt, P.C.

[57] ABSTRACT

Objects of the invention is to provide an air freshner composition which has both excellent functional properties such as shrinkage with the passage of time, clear end point and the like and excellent visual decorativeness due to transparency and is used in a space where an offensive smell is generated, such as the interior of rooms including a toilet room, the interior of automobiles and the like. A transparent gelatin gel type air freshner composition is prepared from gelatin, a gelatin cross-linking agent, water, a perfume, a perfume solvent and a surface active agent as starting materials.

6 Claims, No Drawings

TRANSPARENT GELATIN GEL TYPE AIR FRESHENER

FIELD OF THE INVENTION

This invention relates to a gel type air freshner which has both excellent functional properties such as shrinkage with the lapse of time, clear end point and the like and excellent visual decorativeness due to transparency and is used in a space where an offensive smell is generated, such as the interior of rooms including a toilet room, the interior of automobiles and the like.

PRIOR ART

In the manifold air freshner of recent years, research and development on aqueous gel type air freshner are now actively conducted by laying stress on certain functional properties such as constant vaporization and clear end point by volumetric shrinkage (namely an effect to inform users that diffusion of an air freshner is completed, by its clearly shrunk volumetric appearance after vaporization in comparison with its appearance before vaporization) and some of them are already provided as commodities. Examples of these aqueous gel type air freshners include (a) an air freshner in which natural agar or carrageenan is used (Japanese Patent Application Kokai No. 54-135229(1979)), (b) an air freshner in which a synthetic water soluble polymer is used (Japanese Patent Application Kokai No. 55-81655(1980)) and (c) a transparent aqueous gel type air freshner obtained by neutralizing a cross-linked acrylic acid polymer (Japanese Patent Application Kokai No. 1-119258 (1989)).

However, these aqueous gel type air freshners still have many problems, because they only possess either excellent functional properties such as constant vaporization and clear end point (for the aforementioned case (a)) or excellent visual decorativeness (for the aforementioned cases (b) and (c)).

Particularly, the aforementioned aqueous gel type air freshner (a) produced from carrageenan is generally used because of its markedly excellent cost performance, excellent functional properties such as constant vaporization, clear end point and the like and easiness to control viscosity, but its appearance is not always satisfactory in terms of transparency as will be described later.

On the other hand, air freshners in which a perfume is contained in ceramic pots or a perfume solution is contained in semitransparent or transparent containers are on the market as commodities whose visual decorativeness is improved by devising containers, but these air freshners have some disadvantages in terms of their functional properties such as unclear end point and leakage of the perfume solution when the container is overturned.

Thus, it is the present situation that an air freshner commodity which has both excellent functional properties and excellent decorativeness has not been realized yet.

The decorativeness-related problem involved in the prior art aqueous gel type air freshners having excellent functional properties is due to the opaque or semitransparent nature of carrageenan and the like used as the base of air freshners, which also causes opaque or semitransparent appearance of the air freshners themselves, so that great concern has been directed toward the development of a base material for air freshners which is transparent and has excellent functional properties.

DISCLOSURE OF THE INVENTION

With the aim of resolving the aforementioned problems, the inventors of the present invention have conducted intensive studies and found that sufficient strength (namely a strength of such a degree that an air freshner can stand by its own ability, and such a strength is necessary to obtain more excellent decorativeness) and thermal resistance at 70° C. (such a thermal resistance is required during storage in summer or when used as an air freshner in the interior of automobiles and the like) can be provided when gelatin is selected as a transparent base material capable of keeping perfumes and subjected to cross-linking treatment using a cross-linking agent. Also the inventors have found that the thus treated gelatin is used as the base material of an aqueous gel type air freshners to produce an aqueous gel type air freshner composition which shows excellent visual decorativeness and transparency without spoiling the excellent functional properties such as constant vaporization, clear end point and the like of the prior art aqueous gel air freshners and is also used to produce excellent cost performance aqueous gel type air freshner compositions because of gelatin's inexpensiveness due to its versatile applications such as adhesives, food, photographs, medicines and the like, and the present invention has been accomplished on the basis of these findings.

Accordingly, the present invention relates to a transparent gelatin gel type air freshner composition comprising gelatin, a cross-linking agent for gelatin, water, a perfume, a controlling solvent of perfume vaporization and a surfactant as starting materials and to an air freshner product in which such an air freshner composition is packed in a container of proper shape.

Firstly, the transparent gelatin gel type air freshner composition of the present invention is described.

Gelatin as one of its starting materials is obtained from bovine bone, bovine hide, pigskin and the like materials, and any gelatin obtained by acid treatment or alkali treatment can be used, but gelatin obtained by acid treatment of pigskin may be used desirably when cost, transparency and the like are taken into consideration.

The gelatin content of the air freshner composition is not particularly limited with the proviso that the object of the present invention can be achieved, but it may be 10% by weight or less, preferably 5% by weight or less, in order to obtain clear end point by volumetric shrinkage. However, since sufficient strength of air freshner composition cannot be obtained when the content is too small, it is necessary to set the content generally to about 1% by weight or more from such a point of view.

According to the present invention, in order to provide sufficient strength and thermal resistance as the base material of the air freshner composition, gelatin is subjected to intermolecular or/and intramolecular cross-linking treatment of its composing protein as described in the foregoing. Examples of the cross-linking agent of gelatin include transglutaminase, potassium alum, formaldehyde, glutaraldehyde and the like. It is difficult to use these generally known gelatin cross-linking agents, excluding transglutaminase, in the field of air freshners because of problems in that they are poisonous substances by themselves, poor solubility of the cross-linking agents causes their precipitation and therefore results in no transparency and excellent decorativeness cannot be obtained due to coloring before or after hardening by cross-linking.

Transglutaminase is an enzyme which catalyzes acyl group transfer reaction of the γ-carboxyamido group of glutamine residues in peptide chains. This transglutaminase forms intramolecular and intermolecular ε-(γ-Glu)-Lys cross-linked bonds when the ε-amino group of lysine residues in protein acts as an acyl receptor. Also, when water functions as an acyl receptor, this enzyme accelerates a reaction in which glutamine residue is converted into glutamic acid residue by deamidation.

By allowing the transglutaminase having such functions to act upon gelatin, a base material of a colorless, transparent gelatin gel type air freshner composition having sufficient strength and thermal resistance as an air freshner is obtained.

As it is universally known, transglutaminase is divided into calcium independent and calcium dependent types. Examples of the former type include those which are originated from microorganisms (for instance, see Japanese Patent Application Kokai No. 1-27471(1989)). Examples of the latter type include those which are originated from guinea pig liver (cf. Japanese Patent Publication Kokoku No. 1-50382(1989)) and from fish (for instance, N. Seki et al., *Nippon Suisangaku Kaishi*, vol.56, no.1, p.125 (1990)). Also included are those which are produced by means of recombinant DNA technology (cf. Japanese Patent Application Kokai Nos. 1-300889(1989), 5-199883(1993), 6-225775(1994)). Of the above examples, transglutaminase of animal origin is well known, but its use in the field of air freshner is difficult because it is extremely expensive due to its impracticability to effect large scale production and its calcium dependency. On the other hand, the aforementioned type of microbial origin is inexpensive in comparison with the animal origin, because it is produced by a fermentation method in which a transglutaminase producing microorganism is cultured, and is calcium independent, so that it can be used in the field of air freshner. In this connection, the calcium dependent type is inferior to the calcium independent type in terms, for example, of its limitation of formulation ranges and its influence upon cross-linking reaction due to calcium ions contained in gelatin. In addition, the microbial transglutaminase has been reported to the Ministry of Public Welfare in accordance with the food sanitation law and recorded in the list of food additives other than chemically synthesized compounds (edited by the Ministry of Public Welfare), so that its safety has been confirmed. Its preparations are on the market under trade names of "Activa TG", "Activa TG-K" and the like.

Amount of the transglutaminase (enzyme preparation) to be used is, in short, an amount by which the object of the present invention is achieved, which can be easily found by those skilled in the art according to each desired case with reference to the examples which will be described later or by carrying out a simple preliminary test, and it may for example be about 0.5 to 100 units per 1 g gelatin protein (cf. the aforementioned Japanese Patent Application Kokai No. 1-27471 for the transglutaminase activity).

According to the present invention, as will be understood from the examples which will be described later, water is used in the form of a mixture solvent with an organic solvent at the time of the swelling of gelatin and preparation of a perfume solution. Though not particularly limited, the water of this case may preferably have a high purity when, the quality of the perfume and storage stability of the air freshner composition are taken into consideration, and its preferred example is purified water obtained by distillation or ion exchange resin treatment.

Amount of water to be used is, in short, an amount by which the object of the present invention is achieved, which can be easily found by those skilled in the art according to each desired case, and it may be 50 to 90% by weight based on the total amount of the air freshner composition of the present invention.

The perfume has no particular limitation, and those which are used in prior art air freshner commodities, such as lime, osmanthus, rose, lemon, lavender and the like, may be used. Though not particularly limited, it may be used in an amount of from 1 to 10% by weight based on the total amount of the air freshner composition of the present invention.

Mainly in order to control vaporization of the perfume, a perfume vaporization controlling solvent can be contained in the gel type air freshner composition of the present invention. Examples of such solvent are water soluble solvents which include alcohols such as methanol, ethanol, propanol and the like, polyhydric alcohols such as ethylene glycol, propylene glycol, glycerol and the like, ethylene glycol alkyl ethers, diethylene glycol alkyl ethers, propylene glycol alkyl ethers and the like, and mixtures of two or more.

Amount of the solvent to be used has no particular limitation, with the proviso that selected amounts are effective in achieving the object of the present invention and do not exert bad influence upon transparency of the air freshner composition of the present invention, and the amount can be easily found by those skilled in the art according to each desired case, which may be 0 to 40% by weight based on the total amount of the air freshner composition of the present invention. When such a perfume vaporization controlling solvent is used, it can be added to a perfume solution (which will be described later).

In order to solubilize perfumes, a surfactant is added to the gelatin gel type air freshner composition of the present invention. Generally known compounds, alone or as a mixture of two or more, can be used as the surfactant, which include anionic surfactants such as a fatty acid salt, an alkyl sulfuric ester salt, an alkylbenzene sulfonate, a polyoxyethylene alkyl or alkyl aryl sulfate and the like, and nonionic surfactants such as a polyoxyethylene alkyl ether, a polyoxyethylene alkyl aryl ether, e.g. a polyoxyethylene alkyl phenyl ether, a sorbitan fatty acid ester, a polyoxyethylene sorbitan fatty acid ester, a polyoxyethylene sorbitol fatty acid ester, a polyoxyethylene castor oil, a polyoxyethylene hydrogenated castor oil and the like.

Amount of surfactant to be used also has no particular limitation, with the proviso that selected amounts are effective in achieving the object of the invention without exerting bad influence upon transparency of the air freshner composition of the present invention, and the amount can be easily found by those skilled in the art according to each desired case, which may be 1 to 15% by weight based on the total amount of the air freshner composition of the present invention.

In addition to the aforementioned starting materials, other materials may be used as occasion demands in preparing the transparent gelatin gel type air freshner composition of the present invention, which include pH adjusting agents such as sodium tetraborate, EDTA, sodium citrate and the like, inorganic salts such as potassium chloride, sodium chloride, potassium sulfate and the like and/or optional dyestuffs such as tar base coloring matters, e.g. nitro dye, azo dye, nitroso dye, triphenylmethane dye, xanthene dye, quinoline dye, anthraquinone dye, indigo dye and the like, as well as fluorescence dyestuffs, natural coloring matters, inorganic pigments and the like. More illustratively, the pH adjusting agent is required, for example when a gelatin solution has a pH value of 5 or less or 9 or more, to adjust its pH value within the range of from 5 to 9, which is the active pH range of transglutaminase, and, in that case, the pH adjustment can be effected by adding the agent to the gelatin solution (which will be described later). The inorganic salt is required for example when it is necessary to improve moisture keeping power of gelatin, and, in that case, it can be added to the gelatin solution. The dyestuff can be used when additional decorativeness is provided to commodities for example by changing color of the air freshner composition depending on the kind of perfume.

There is no particular difficulty in preparing the transparent gelatin gel type air freshner composition of the present invention making use of the starting materials described above. For example, it can be prepared by stirring and mixing all starting materials to be used at once and keeping the thus obtained mixture under such conditions that transglutaminase can act upon gelatin.

However, as will be shown in examples later, it is desirable from the viewpoint of production process to separately prepare a gelatin solution and a perfume solution in advance and to mix these two solutions thereafter. In that case, transglutaminase is added to the perfume solution, in order to prevent reaction of gelatin with transglutaminase during mixing and dissolution steps of other starting materials. By mixing the gelatin solution with the perfume solution, action of transglutaminase upon gelatin is effected. As described in the foregoing, in such a preparation method, a pH adjusting agent, an inorganic salt and or a dyestuff can be optionally added to the gelatin solution or perfume solution.

When the transparent gelatin gel type air freshner composition of the present invention is made into an air freshner product, it must be contained in a container as a matter of course as in conventional air freshner products, and an important factor in that case is that such a container can make the most of the aforementioned characteristics of the air freshner composition of the present invention, namely excellent functional properties, such as shrinkage with the lapse of time, clear end point and the like and excellent visual decorativeness due to transparency. For this purpose, however, the container for use in the inclusion of the air freshner composition of the present invention is not necessarily transparent as can be easily understood by those skilled in the art. Also, it is desirable as a matter of course to make the air freshner composition into a commodity having excellent visual decorativeness including its shape, depending on the place where it is used.

EXAMPLES

The following describes the present invention further in detail with reference to examples and comparative examples which, as a matter of course, do not restrict the scope of the present invention.

Example 1

A 50 g portion of commercially available dry gelatin "Gelatin PS-260" (manufactured by Systems Bio-Industries) was added to 550 g of purified water to effect its swelling and then heated at 50° C. to prepare a gelatin solution. Another container was charged with 50 g of ethanol, 309 g of purified water, 10 g of polyoxyethylene (10 mol) alkyl phenyl ether, 10 g of polyoxyethylene (40 mol) hydrogenated castor oil, 1 g of transglutaminase "Activa TG" (manufactured by Ajinomoto; specific activity: 1.000 units/1 g) and 20 g of a osmanthus perfume "OSMANTHUS 95017" (manufactured by Nihon Firmenich K.K.), and these materials were thoroughly mixed with stirring to effect dissolution of said perfume, thereby obtaining a perfume solution.

Next, the thus prepared perfume solution was added to the gelatin solution obtained above, and the resulting mixture was thoroughly stirred and then heated at 50° C. for 5 minutes. Finally, in order to obtain more excellent decorativeness, the resulting solution was poured into a mold and allowed to stand at 5° C. for 3 hours in a refrigerator to obtain a transparent gelatin gel air freshner composition of the present invention.

Example 2

A gelatin solution was prepared in the same manner as described in Example 1, except that the gelatin was changed to a commercially available dry gelatin "Gelatin PS-240" (manufactured by Systems Bio-Industries). Another container was charged with 100 g of diethylene glycol monoethyl ether, 259.5 g of purified water, 10 g of polyoxyethylene (10 mol) alkyl phenyl ether, 10 g of polyoxyethylene (60 mol) hydrogenated castor oil, 0.5 g of the same transglutaminase "Activa TG" as used in Example 1 and 20 g of the same osmanthus perfume "OSMANTHUS 95017" as used in Example 1, and these materials were thoroughly mixed with stirring to effect dissolution of said perfume, thereby obtaining a perfume solution.

Next, the thus prepared perfume solution was added to the gelatin solution obtained above, and then the resulting mixture was treated in the same manner as described in Example 1 to obtain a transparent gelatin gel air freshner composition of the present invention.

Example 3

7.35 g of trisodium citrate dihydrate as a pH adjusting agent was dissolved in 560 g of purified water, to which 40 g of "Gelatin PS-260" was added to effect its swelling and then heated at 50° C. to prepare a gelatin solution. Another container was charged with 100 g of 3-methyl-3-methoxybutanol, 252.15 g of purified water, 10 g of polyoxyethylene (20 mol) alkyl phenyl ether, 10 g of polyoxyethylene (60 mol) hydrogenated castor oil, 0.5 g of the same transglutaminase "Activa TG" as used in Example 1 and 30 g of the same osmanthus perfume as used in Example 1, and these materials were thoroughly mixed with stirring to effect dissolution of said perfume, thereby obtaining a perfume solution.

Next, the thus prepared perfume solution was added to the gelatin solution obtained above, and then the resulting mixture was treated in the same manner as described in Example 1 to obtain a transparent gelatin gel air freshner composition of the present invention.

Comparative Example 1

A gelatin gel air freshner composition was prepared in the same manner as described in Example 1, except that 305 g of purified water was used instead of 309 g of purified water in preparing the perfume solution and 5 g of potassium alum was used as a cross-linking agent instead of 1 g of the transglutaminase "Activa TG". This gelatin gel air freshner composition contained crystalline insoluble matters.

Comparative Example 2

A gelatin gel air freshner composition was prepared in the same manner as described in Comparative Example 1, except that 5 g of glutaraldehyde was used as a cross-linking agent instead of 5 g of potassium alum. This gelatin gel air freshner composition was transparent but yellow.

Comparative Example 3

A 20 g portion of a commercially available carrageenan "Carrageenan Air-10" (manufactured by Marine Science)

was added to 885 g of purified water and heated at 75° C. to prepare a carrageenan solution. Separately from this, a container was charged with 25 g of purified water, 30 g of propylene glycol, 5 g of potassium chloride, 30 g of a perfume and 5 g of polyethylene glycol (20) sorbitan monostearate, and these materials were thoroughly mixed to prepare a perfume solution.

The thus prepared perfume solution was added to the carrageenan solution which was heated at 60° C., and the mixture was thoroughly stirred, poured into a mold and then cooled to room temperature to obtain a carrageenan gel air freshner composition.

Evaluation Example 1

Appearances and vaporization performance of the aqueous gel type air freshner compositions obtained in Examples 1 to 3 and Comparative Examples 1 to 3 were evaluated by the method shown in Table 1 below.

TABLE 1

| Evaluation method | | |
|---|---|---|
| Appearance | Transparency: | judged by the naked eye (○: transparent, ×: opaque) |
| | Color: | judged by the naked eye |
| Vaporization | Allowed to stand at room temperature in an open space for a period of time corresponding to the number of used days of the air freshner composition, and evaluated as % by weight after use based on its weight before use. | |

The results are shown in Table 2 below.

TABLE 2

| | Results of evaluation | | | | | |
|---|---|---|---|---|---|---|
| | Evaluation items | | | | | |
| | Appearances | | Vaporization (% by weight) | | | |
| | Trans- | | Time (week) after use | | | |
| Samples | parency | Color | 1 | 2 | 3 | 4 |
| Ex. 1 | ○ | colorless | 55.3 | 24.2 | 16.9 | 12.1 |
| Ex. 2 | ○ | colorless | 63.4 | 30.2 | 21.5 | 12.8 |
| Ex. 3 | ○ | colorless | 58.6 | 24.6 | 19.8 | 14.3 |
| Comparative Ex. 1 | × | colorless | 53.4 | 24.3 | 14.6 | 13.5 |
| Comparative Ex. 2 | ○ | yellow | 55.1 | 25.4 | 14.4 | 12.4 |
| Comparative Ex. 3 | × | milk white | 61.2 | 22.4 | 12.1 | 8.9 |

As can be understood from Table 2, the transparent gelatin type air freshner compositions of the present invention (Examples 1 to 3) are excellent, because they have a colorless, transparent appearance which cannot be provided by the gelatin gel type air freshner composition in which a generally well known gelatin cross-linking agent potassium alum (Comparative Example 1) or glutaraldehyde (Comparative Example 2) is used or by the aqueous gel type air freshner composition in which carrageenan is used as the base material (Comparative Example 3), while they show almost the same vaporization performance as in the aqueous gel type air freshner composition in which generally used carrageenan is adopted as the base material (Comparative Example 3).

ADVANTAGES OF THE INVENTION

The present invention has rendered possible production of an aqueous gel type air freshner which has excellent functional properties such as constant vaporization, clear end point and the like, simultaneously shows excellent visual decorativeness due to contribution of transparency, and is also excellent in cost performance.

We claim:

1. A transparent gelatin gel type air freshener composition consisting essentially of gelatin, a transglutaminase gelatin cross-linking agent, water, a perfume and a surface active agent.

2. The transparent gelatin gel type air freshener composition according to claim 1 wherein the cross-linking agent is a calcium independent transglutaminase.

3. The transparent gelatin gel type air freshener composition according to claim 1 or 2 which further comprises a perfume vaporization controlling solvent, a pH controlling agent, an inorganic salt and/or a dyestuff.

4. An air freshener product in which the air freshener composition of claim 3 is contained in a container.

5. An air freshener product in which the air freshener composition of claim 1 is contained in a container.

6. An air freshener product in which the air freshener composition of claim 2 is contained in a container.

* * * * *

UNITED STATES PATENT AND TRADEMARK OFFICE
CERTIFICATE OF CORRECTION

PATENT NO.      : 5,750,498
DATED           : May 12, 1998
INVENTOR(S)     : Takahiko Soeda et al.

It is certified that error appears in the above-identified patent and that said Letters Patent is hereby corrected as shown below:

<u>Column 8,</u>
Line 43, "composition of claim 3" should read -- composition of claim 1 --;
Line 45, "composition of claim 1" should read -- composition of claim 2 --;
Line 47, "composition of claim 2" should read -- composition of claim 3 --.

Signed and Sealed this

Sixteenth Day of July, 2002

Attest:

Attesting Officer

JAMES E. ROGAN
*Director of the United States Patent and Trademark Office*